(12) United States Patent
Bounouar et al.

(10) Patent No.: US 11,953,484 B2
(45) Date of Patent: Apr. 9, 2024

(54) METHOD FOR SETTING AN AIRBORNE MOLECULAR CONTAMINATION MEASUREMENT STATION, AND MEASUREMENT STATION

(71) Applicant: PFEIFFER VACUUM, Annecy (FR)

(72) Inventors: Julien Bounouar, Annecy (FR); Olivier Le Barillec, Annecy (FR); Nicolas Chapel, Sales (FR)

(73) Assignee: PFEIFFER VACUUM, Annecy (FR)

( * ) Notice: Subject to any disclaimer, the term of this patent is extended or adjusted under 35 U.S.C. 154(b) by 252 days.

(21) Appl. No.: 17/425,061

(22) PCT Filed: Jan. 22, 2020

(86) PCT No.: PCT/EP2020/051539
§ 371 (c)(1),
(2) Date: Jul. 22, 2021

(87) PCT Pub. No.: WO2020/160910
PCT Pub. Date: Aug. 13, 2020

(65) Prior Publication Data
US 2022/0099646 A1    Mar. 31, 2022

(30) Foreign Application Priority Data

Feb. 5, 2019    (FR) ........................... 1901091

(51) Int. Cl.
*G01N 33/00*    (2006.01)
*G01N 1/22*    (2006.01)
(Continued)

(52) U.S. Cl.
CPC ........... *G01N 33/0075* (2013.01); *G01N 1/22* (2013.01); *G01N 1/26* (2013.01); *G05D 7/0658* (2013.01)

(58) Field of Classification Search
CPC ........ G01N 33/0075; G01N 1/22; G01N 1/26; G05D 7/0658
See application file for complete search history.

(56) References Cited

U.S. PATENT DOCUMENTS

2003/0235926 A1* 12/2003 Knollenberg ........ G01N 29/022
436/178
2005/0217391 A1* 10/2005 Gamache ............ G01N 1/2247
73/863
(Continued)

FOREIGN PATENT DOCUMENTS

GB    2 390 161 A    12/2003
KR    10-2014-0026811 A    3/2014
(Continued)

OTHER PUBLICATIONS

International Search Report dated Apr. 23, 2020 in PCT/EP2020/051539 filed on Jan. 22, 2020, 2 pages.
(Continued)

*Primary Examiner* — Kristina M Deherrera
*Assistant Examiner* — Fatemeh Esfandiari Nia
(74) *Attorney, Agent, or Firm* — Oblon, McClelland, Maier & Neustadt, L.L.P.

(57) ABSTRACT

A setting method includes setting the conductances of the controllable restrictions of an airborne molecular contamination measurement station. The setting method includes an initial identification step, prior to the carrying-out of an airborne molecular contamination measurement step, and during which the sampling line that has the lowest conductance when the conductance of the controllable restriction of the said sampling line is set to its maximum value is determined, and an initial conductance-setting step prior to the carrying-out of the measurement step and after the initial identification step, and during which the conductances of the controllable restrictions are set to make them correspond to (Continued)

the lowest conductance determined in the initial identification step. Further, a measurement station is provided for measuring airborne molecular contamination.

10 Claims, 2 Drawing Sheets

(51) Int. Cl.
  *G01N 1/26* (2006.01)
  *G05D 7/06* (2006.01)

(56) References Cited

U.S. PATENT DOCUMENTS

| | | | |
|---|---|---|---|
| 2006/0234621 A1* | 10/2006 | Desrochers | G01N 1/26 |
| | | | 702/50 |
| 2017/0315107 A1 | 11/2017 | Chou et al. | |
| 2019/0137126 A1* | 5/2019 | Desrochers | F24F 11/0001 |

FOREIGN PATENT DOCUMENTS

| | | | |
|---|---|---|---|
| WO | WO 01/79809 A1 | 10/2001 | |
| WO | WO-2015087044 A1 * | 6/2015 | E21B 47/003 |

OTHER PUBLICATIONS

French Search Report dated Nov. 13, 2019, in French Patent Application No. 1901091, 9 pages.

\* cited by examiner

METHOD FOR SETTING AN AIRBORNE MOLECULAR CONTAMINATION MEASUREMENT STATION, AND MEASUREMENT STATION

The present invention relates to a method for setting an airborne molecular contamination measurement station intended in particular to monitor concentrations of molecular contamination in the atmosphere of clean rooms, such as the clean rooms of factories that manufacture semiconductors. The present invention also relates to such a measurement station.

In the semiconductor manufacturing industry, the substrates, such as semiconductor wafers or photomasks, need to be protected from airborne molecular contamination (AMC) in order to prevent such contamination from damaging the chips or electronic circuits of the substrates. For that purpose, the substrates are contained in atmospheric transport and storage boxes that allow the substrates to be transported from one piece of equipment to another or stored between two manufacturing steps. Moreover, the transport boxes and the equipment are located inside clean rooms in which the level of particles is minimized and the temperature, humidity and pressure are kept at precise levels.

The airborne gaseous species may originate from various sources and be of various natures, and include, for example, acids, bases, condensable elements and dopants. These molecules may originate from the air inside the semiconductor manufacturing plant or may notably be released by the semiconductor wafers which have undergone prior manufacturing operations.

Gas analyzers present in the clean rooms allow real-time evaluation of the concentration of the airborne gaseous species, notably that of the humidity and of a few acids. The concentrations measured are sometimes very low, such as of the order of ppm or ppb. These gas analyzers measure the gaseous atmosphere surrounding them and it is therefore necessary to provide a gas analyzer in each clean-room zone that is to be tested.

There is a need to increase the number of gaseous species measured and the number of test zones in order to reduce the risks of substrate contamination. However, increasing the number of analyses per zone and increasing the number of these zones that are to be tested soon makes this solution very costly.

In order to reduce costs, a measurement unit that combines various analyses has been proposed. The unit is equipped with several inlet ports each addressing a particular test zone of the clean room.

The measurements are carried out in sequence, namely by measuring each test zone in turn.

The problem with sequential measurements is that an abnormal concentration of one gaseous species in one test zone can be detected only when a measurement in that test zone is ordered. In fact, many minutes may elapse before a potential risk of contamination in one zone of the clean room becomes apparent.

Another solution is to measure the concentrations of gaseous species simultaneously in a subset of different zones to be tested. It is then possible quickly to detect whether a mean concentration of a gas in this subset has exceeded an admissible threshold. When an abnormal concentration is detected, a search is made through the subset to determine which sampling line is affected, for example by sequencing through the subset.

However, that solution does not take into account the various conductances between the sampling lines. Specifically, these lines do not all have the same length. Certain lines may be very short and others very long. The pumping flow rates may therefore exhibit large disparities between the lines. Thus, in simultaneously measuring in several sampling lines, the contribution of the lines is inconsistent. It is possible that the measurement obtained might not correspond to the mean of the concentration of the gases in the subset of zones because it has been weighted according to the conductance of the lines, the lines with better conductance, generally the shortest ones, making a greater contribution.

It is one of the objects of the present invention to propose a measurement station and a method for setting the conductances of the controllable restrictions of a measurement station, that at least partially address one of the aforementioned disadvantages.

To that end, one subject of the invention is a setting method for setting the conductances of the controllable restrictions of an airborne molecular contamination measurement station, the measurement station comprising:
  at least one gas analyzer, and
  at least two sampling lines which are connected to a common line which is connected to an inlet of the at least one gas analyzer, each sampling line comprising a controllable restriction having a conductance that can be set between a minimum value and a maximum value,
    characterized in that the setting method comprises:
      an initial identification step, prior to the carrying-out of an airborne molecular contamination measurement step, and during which the sampling line that has the lowest conductance when the conductance of the controllable restriction of the said sampling line is set to its maximum value is determined, and
      an initial conductance-setting step prior to the carrying-out of the measurement step and after the initial identification step, and during which the conductances of the controllable restrictions are set to make them correspond to the lowest conductance determined in the initial identification step.

Thus, whatever the sampling lines in which a measurement is carried out simultaneously, the contribution made by each line is balanced with respect to the others without being dependent on the conductance of the line. The measurement obtained may be close to the true mean measurement of the test zones. The one same alert threshold for the level of concentration of gaseous species can thus be used for all the sampling lines tested simultaneously.

The setting method may further comprise one or more features which are described hereinafter, considered alone or in combination.

According to one exemplary embodiment, the measurement station further comprises at least two controllable valves, one controllable valve being arranged on each of the sampling lines.

According to one exemplary embodiment, the measurement station comprises a pressure sensor arranged on the common line to measure the pressure in the common line which is connected to the inlet of the at least one gas analyzer.

According to one exemplary embodiment, the measurement station comprises a sampling pump which is connected to the common line, and so as to sample a gas that is to be analyzed in a sampling line and so that it is analyzed by the at least one gas analyzer.

According to one exemplary embodiment, during the initial identification step:

the controllable valve of each sampling line is opened in turn, the conductance of the controllable restriction being set to the maximum value, the other controllable valves being closed, and the pressure in the common line is measured, the sampling line having the lowest conductance being the one for which the pressure measurement is the lowest.

According to one exemplary embodiment, during the initial conductance-setting step, the controllable valve of the sampling line of the controllable restriction that is to be set is opened, the other controllable valves of the other sampling lines being closed, and the conductance of the controllable restriction is set so that the pressure measured in the common line corresponds to the lowest pressure measurement corresponding to the sampling line having the lowest conductance.

For example, during the initial conductance-setting step, the conductance of the controllable restriction is set so that it corresponds to at most +/−10%, such as at most +/−5%, of the lowest conductance.

The initial conductance-setting step may be repeated for all the controllable restrictions other than that of the sampling line that has the lowest conductance.

The initial identification step and/or the initial conductance-setting step are carried out for a first time when the measurement station is started up, and then at each maintenance operation and/or are repeated regularly.

The initial identification step may be carried out each time a sampling line is modified, the initial conductance-setting step being repeated for all the sampling lines if the conductance of the modified sampling line, as determined in the initial identification step, becomes the lowest. If the conductance of the modified sampling line is not the lowest then only the conductance of the controllable restriction of the modified sampling line is set to make it correspond to the lowest conductance determined in the initial identification step, since the other conductances have already been set.

During the airborne molecular contamination measurement step a measurement may be taken in several sampling lines simultaneously. The simultaneous measurements in several sampling lines may be carried out in a subset of the sampling lines.

Another subject of the invention is a measurement station for measuring airborne molecular contamination, comprising:

at least one gas analyzer, and at least two sampling lines which are connected to a common line which is connected to an inlet of the at least one gas analyzer, a measurement being taken in several sampling lines simultaneously during a measurement step, characterized in that:

each sampling line comprises a controllable restriction having a conductance that can be set between a minimum value and a maximum value, the conductances of the controllable restrictions of the sampling lines are set by a setting method as described hereinabove to correspond to the maximum conductance of the sampling line that has the lowest conductance.

According to one exemplary embodiment, the walls of the controllable restrictions in fluidic communication with the gases may be made from one or more fluoropolymer materials, such as a perfluoroalkoxy (also referred to as PFA) polymer or of polytetrafluoroethylene (also referred to as PTFE).

The measurement station may further comprise:

at least two controllable valves, one controllable valve being arranged on each of the sampling lines, a sampling pump which is connected to the common line, and a pressure sensor arranged on the common line, to measure the pressure in the common line that is connected to the inlet of the at least one gas analyzer.

The measurement station may also comprise a control unit which is connected to the controllable valves and to the pressure sensor, the control unit being configured to operate the opening or the closing of the controllable valves.

INTRODUCTION TO THE DRAWINGS

Further advantages and features will become apparent from reading the following description of one particular, but nonlimiting, embodiment of the invention and from studying the attached drawings in which.

In these figures, the elements that are identical bear the same reference numerals.

The following embodiments are examples. Although the description refers to one or more embodiments that does not necessarily mean that each reference relates to the same embodiment or that the features apply only to one single embodiment. Simple features from various embodiments may also be combined or interchanged to create other embodiments.

Figure 1:
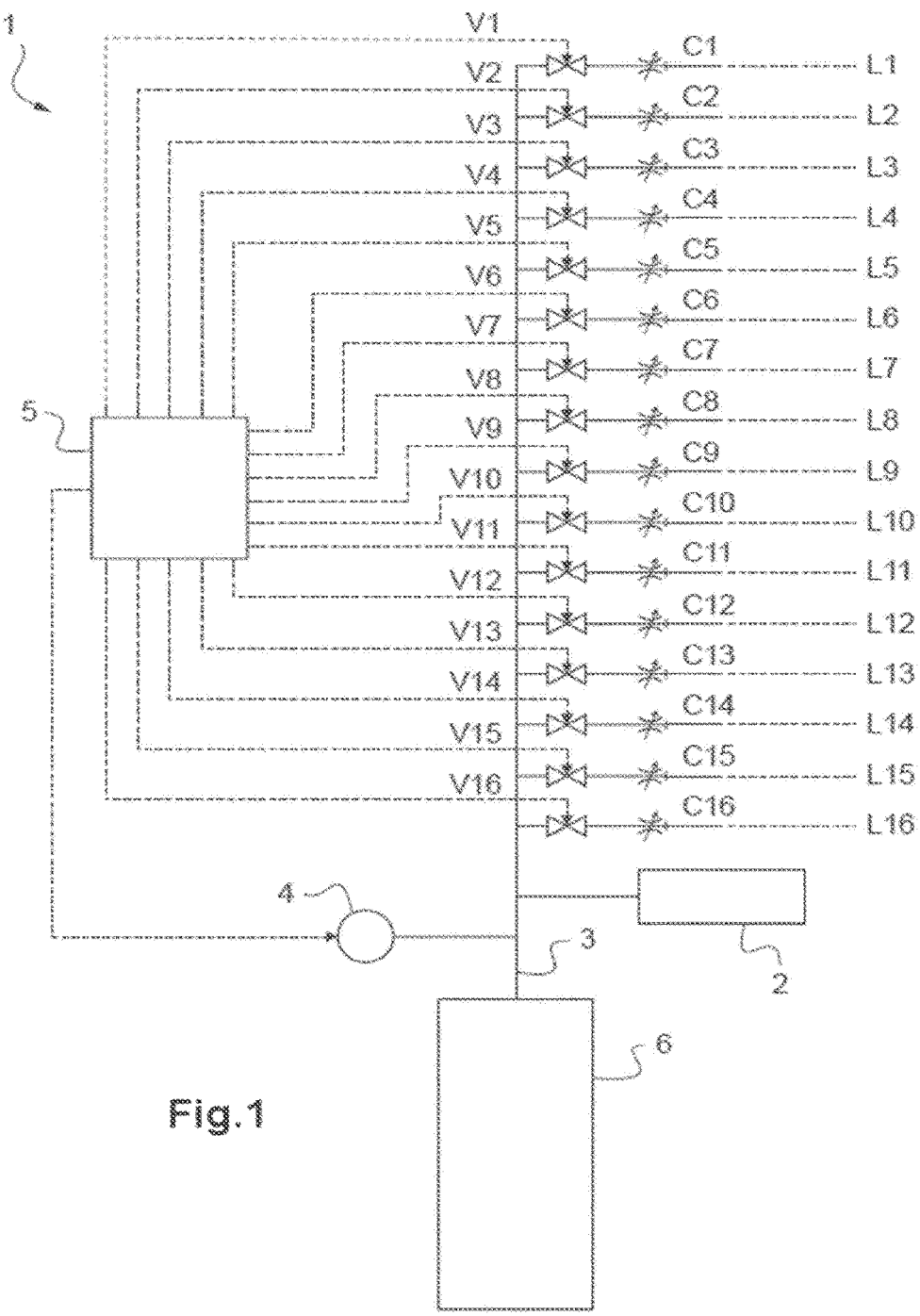
FIG. 1 depicts a schematic view of elements of an airborne molecular contamination measurement station.

FIG. 1 shows elements of an airborne molecular contamination measurement station 1 intended in particular to monitor concentrations of molecular contamination in the atmosphere of clean rooms, such as the clean rooms of semiconductor manufacturing facilities.

The measurement station 1 comprises at least one gas analyzer 2 and at least two sampling lines L1-L16 which are connected to a common line 3 which is connected to the inlet of the at least one gas analyzer 2. The gas analyzer 2 may thus be placed in communication with each sampling line L1-L16. The end of each sampling line L1-L16 is situated in a test zone at ambient pressure, namely at atmospheric pressure, for example in a distinct area of a clean room.

Each sampling line L1-L16 comprises a controllable restriction C1-C16 having a conductance that can be set between a minimum value and a maximum value.

The measurement station 1 may further comprise at least two controllable valves V1-V16, one controllable valve V1-V16 being arranged on each sampling line L1-L16. The measurement station 1 may comprise a pressure sensor 4 arranged on the common line 3 to measure the pressure in the common line 3. It may further comprise a control unit 5 which is connected to the controllable valves V1-V16 and to the pressure sensor 4.

According to one exemplary embodiment, the measurement station 1 comprises a sampling pump 6 which is connected to the common line 3. The gas to be analyzed may thus be sampled in the sampling lines to be analyzed by the at least one gas analyzer 2.

The sampling pump may be arranged in the same housing as the at least one gas analyzer 2.

The gas analyzer 2 makes it possible to measure the concentration of at least one gaseous species in real time, namely with a measurement duration of under a few seconds, or else of a few minutes, for low concentrations below ppm or ppb. The gaseous species measured is, for example, an acid, such as hydrofluoric acid HF or hydrochloric acid HCl or a solvent such as PGMEA (propylene glycol methyl ether). According to another example, the gaseous species is ammonia $NH_3$. A gas analyzer 2 may be designed to measure a distinct gaseous species or a group of distinct gaseous species.

A controllable restriction is a passage for the gases the conductance of which is variable. The conductance is the inverse of the resistance to flow. It is the ratio between the flow of gas circulating through the passage and the pressure difference across the two ends of the passage.

The conductances of the controllable restrictions C1-C16 can be varied for example manually or using an associated controller. According to another example, the controllable restrictions can be controllable by the control unit 5.

The controllable restrictions C1-C16 are produced for example in the form of valves or flow regulators.

According to one exemplary embodiment, the walls of the controllable restrictions C1-C16 in fluidic communication with the gases are made from materials that limit the adhesion of the gaseous species to the walls, such as of one or more fluoropolymer materials, such as of perfluoroalkoxy (also referred to as PFA) polymer or of polytetrafluoroethylene (also referred to as PTFE).

The sampling lines L1-L16 and the walls of the controllable valves V1-V16 may also be made from such materials.

The sampling lines L1-L16 connect the measurement station 1 to distinct test zones. The length of the sampling lines L1-L16 may vary between the various test zones that are to be combined and may be several tens of meters, such as a length of between 40 and 300 meters.

The controllable valves V1-V16 are, for example, electrically-operated valves or pneumatic valves. They can be operated as all-or-nothing (open or closed) by the control unit 5.

During a measurement of the airborne molecular contamination, a measurement may be taken in several sampling lines L1-L16 simultaneously.

The conductances of the controllable restrictions of the sampling lines L1-L16 are set by a setting method 100 so that they correspond to the maximum conductance of the sampling line that has the lowest conductance.

Figure 2:
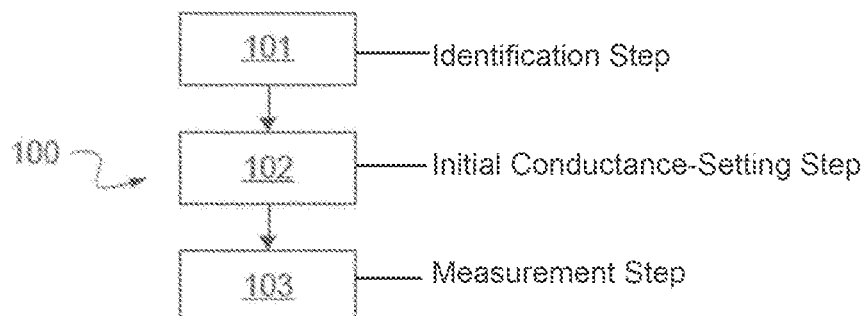
FIG. 2 depicts a schematic view of a method for setting conductances of controllable restrictions of the measurement station of FIG. 1.

The setting method 100 comprises an initial identification step 101 and an initial conductance-setting step 102, these steps being performed prior to the carrying-out of a measurement step 103 (FIG. 2).

In the initial identification step 101, the sampling line L1-L16 having the lowest conductance when the conductance of the controllable restriction C1-C16 of the said sampling line L1-L16 is set to its maximum value is determined (FIG. 2).

For example, the controllable valve V1-V16 of each sampling line L1-L16 in turn is opened and the conductance of the controllable restriction C1-C16 is set to the maximum value, the other controllable valves V1-V16 being closed, and the pressure in the common line 3 at the inlet of the at least one gas analyser 2 is measured. Given that, for each sampling line L1-L16, it is the same sampling pump 6 that is used, the pressure measurement in the common line 3 at the inlet of the gas analyser 2 is equivalent to a measurement of the conductance of the sampling line (Q=C*DeltaP) where C is the conductance of the passage of the controllable restriction Q is the flow of gas (or "throughput") circulating through the passage of the conductance DeltaP is the pressure difference across the two ends of the passage of the conductance (the difference between upstream pressure and downstream pressure). As a result, the sampling line L1-L16 that has the lowest conductance is the one for which the pressure measurement in the common line 3 is the lowest.

Figure 3:
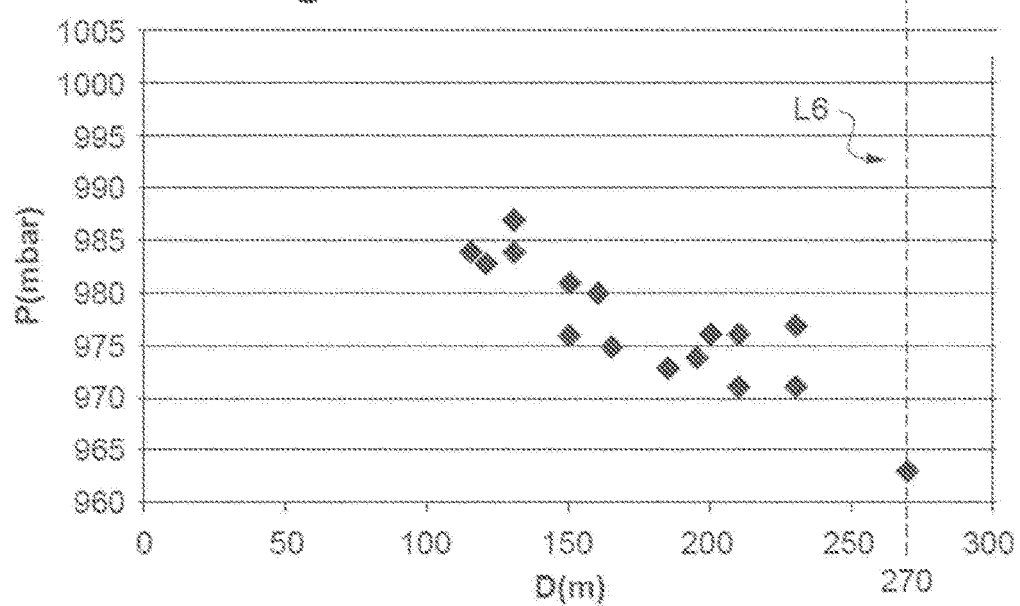
FIG. 3 is a graph showing one example of pressure measurements (in mbar) in the common line that is connected to the sampling pump, which are obtained for sampling lines of the measurement station of FIG. 1, as a function of the length (in meters on the abscissa axis) of the sampling lines.

The graph of FIG. 3 thus illustrates an example of pressure measurements obtained during an initial identification step 101.

The absolute pressure measured in the common line 3 for each opening of a controllable valve with the conductance of the controllable restriction set to the maximum value and with the other valves closed is shown on the ordinate axis.

It may be seen from the graph that the pressure in each of the sixteen sampling lines L1-L16 decreases with increase in length of the sampling line L1-L16 (on the abscissa axis). The greater the length of the sampling line, the lower the observed pressure, for the same line diameter. The sampling line L1-L16 having the lowest conductance is the one that has the lowest pressure measurement. In this example this is the sampling line L6 that has a length of 270 meters.

Once the sampling line L6 that has the lowest conductance has been identified, the controllable restrictions C1-C5, C7-C16 of the other sampling lines L1-L5, L7-L16 can be set.

During the initial conductance-setting step 102, the conductances of the controllable restrictions are set to make them correspond to the lowest conductance determined in the initial identification step 101, such as to at most +/−10%, such as to at most +/−5%, of the lowest conductance (FIG. 2).

In this step 102, the controllable valve of the sampling line L1-L5, L7-L16 of the controllable restriction that is to be set is open for example, the other controllable valves of the other sampling lines being closed, and the conductance of the controllable restriction is set so that the pressure measured in the common line 3 corresponds to the lowest pressure measurement corresponding to the sampling line that has the lowest conductance.

For example, the conductances of the controllable restrictions of the other sampling lines L1-L16 are set to correspond to at most +/−10%, such as at most +/−5%, of the conductance of the lowest-conductance sampling line or, in other words, the conductances are regulated so that they are the same as the lowest conductance, to within 10% or 5%.

The initial conductance-setting step 102 can be repeated for all the controllable restrictions other than the one of the sampling line that has the lowest conductance. The conductances of the controllable restrictions of the sampling lines L1-L5, L7-L16 other than the sampling line L6 that has the lowest conductance may thus each be set in turn.

The initial steps 101, 102 can be carried out for a first time when the measurement station 1 is started up, and then at each maintenance operation and/or repeated regularly.

The initial identification step 101 may be carried out each time the sampling line is modified, the initial conductance-setting step 102 being repeated for all the sampling lines if the conductance of the modified sampling line as determined in the initial identification step 101 becomes the lowest.

During a measurement step 103, the flow rate of sampling by the sampling pump 6 is constant and identical to the initial steps 101, 102.

The simultaneous measurements in several sampling lines L1-L16 may be taken in a subset of sampling lines. Thus, the controllable valve V6 of the sampling line L6 that has the lowest conductance is able not to be opened during a measurement step 103 in a subset that does not include it.

In the case of controllable restrictions that can be operated, it is possible to perform the initial steps 101, 102 in a subset in order to determine which sampling line of the subset has the lowest conductance and set the conductances of the controllable restrictions of the other sampling lines of the subset to make them correspond to the lowest conductance.

Thus, whatever the sampling lines in which a measurement is taken simultaneously, the contribution made by each line is balanced against the other lines without being dependent on the conductance of the line. The measurement obtained may be close to the true mean measurement of the test zones. The one same alarm threshold for the level of concentration of gaseous species can thus be used for all the sampling lines of the subset to be tested.

Furthermore, it is possible to detect potential errors in connection of the sampling lines L1-L16 to the measurement station 1 notably when, in the initial identification step 101, the pressure measurement is not consistent with the known length of the sampling line.

The invention claimed is:

1. A setting method for setting conductances of controllable restrictions of an airborne molecular contamination measurement station, the measurement station includes at least one gas analyser, and at least two sampling lines which are connected to a common line which is connected to an inlet of the at least one gas analyser, each sampling line comprising a controllable restriction having a conductance that can be set between a minimum value and a maximum value, the setting method comprising:
   an initial identification step, prior to carrying-out of an airborne molecular contamination measurement step, and during which a sampling line that has a lowest conductance when the conductance of the controllable restriction of the at least two sampling lines is set to its maximum value, is determined; and
   an initial conductance-setting step prior to carrying-out of the measurement step and after the initial identification step, and during which the conductances of the controllable restrictions are set to make them correspond to the lowest conductance determined in the initial identification step.

2. The setting method according to claim 1, wherein the measurement station further includes at least two controllable valves, one controllable valve being arranged on each of the sampling lines, a sampling pump which is connected to the common line, and a pressure sensor arranged on the common line,
   wherein during the initial identification step:
   the controllable valve of each sampling line is opened in turn, the conductance of the controllable restriction being set to the maximum value, the other controllable valves being closed, and
   the pressure in the common line is measured, the sampling line having the lowest conductance being the one for which the pressure measurement is the lowest.

3. The setting method according to claim 1, the measurement station further comprising at least two controllable valves, one controllable valve being arranged on each sampling line and a pressure sensor arranged on the common line to measure the pressure in the common line which is connected to the inlet of the at least one gas analyser, wherein during the initial conductance-setting step, the controllable valve of the sampling line of the controllable restriction that is to be set is opened, the other controllable valves of the other sampling lines being closed, and the conductance of the controllable restriction is set so that the pressure measured in the common line corresponds to the lowest pressure measurement corresponding to the sampling line having the lowest conductance.

4. The setting method according to claim 1, wherein during the initial conductance-setting step, the conductance of the controllable restriction is set so that it corresponds to at most +/−10% of the lowest conductance.

5. The setting method according to claim 1, wherein the initial conductance-setting step is repeated for all the controllable restrictions other than that of the sampling line that has the lowest conductance.

6. The setting method according to claim 1, wherein the initial identification step and/or the initial conductance-setting step are carried out for a first time when the measurement station is started up, and then at each maintenance operation and/or are repeated regularly.

7. The setting method according to claim 1, wherein the initial identification step is carried out each time a sampling line is modified, the initial conductance-setting step being repeated for all the sampling lines if the conductance of the modified sampling line, as determined in the initial identification step, becomes the lowest.

8. The setting method according to claim 1, wherein during the airborne molecular contamination measurement step a measurement is taken in several sampling lines simultaneously.

9. The setting method according to claim 1, wherein the simultaneous measurements in several sampling lines are carried out in a subset of the sampling lines.

10. The setting method according to claim 1, wherein during the initial conductance-setting step, the conductance of the controllable restriction is set so that it corresponds to at most +/−5% of the lowest conductance.

* * * * *